United States Patent [19]

Yoshikazu et al.

[11] 4,191,810
[45] Mar. 4, 1980

[54] PROCESS FOR THE PRODUCTION OF IMMOBILIZED GLUCOSE ISOMERASE

[75] Inventors: Nakajima Yoshikazu; Suzuki Kazumasa, both of Okayama; Makino Tsuyoshi, Kamakura, all of Japan

[73] Assignee: Mitsui Sugar Co., Ltd., Tokyo, Japan

[21] Appl. No.: 856,604

[22] Filed: Dec. 1, 1977

[30] Foreign Application Priority Data

Dec. 3, 1976 [JP] Japan .................. 51/144639

[51] Int. Cl.² ............................................... C07G 7/02
[52] U.S. Cl. .................................... 435/177; 435/234
[58] Field of Search .......... 195/63, 68, 31 F, DIG. 11

[56] References Cited

U.S. PATENT DOCUMENTS

| 3,838,007 | 9/1974 | van Velzen ............. 195/68 |
| 3,980,521 | 9/1976 | Amotz et al. ........... 195/31 F |
| 4,001,082 | 1/1977 | Tsumura et al. ........ 195/31 F |
| 4,025,389 | 5/1977 | Poulsen et al. ......... 195/31 F |
| 4,116,771 | 9/1978 | Amotz et al. ........... 195/63 |

*Primary Examiner*—Lionel M. Shapiro
*Attorney, Agent, or Firm*—Kane, Dalsimer, Kane, Sullivan and Kurucz

[57] ABSTRACT

Immobilized glucose isomerase preparation is prepared from microbial cells of Actinomycetes having glucose isomerase activity by the following procedures:

A liquid culture of said microorganism is adjusted to a pH value of 6 to 9, heated to a temperature of 70° to 80° C., held for 1 to 20 minutes at the temperature and cooled rapidly. Then the microbial cells are harvested from the culture by filtration or centrifugation, frozen, subsequently thawed, and mixed with gelatin or sodium caseinate in an amount of 2 to 10% based on the dry substance of the treated cells. The mixture is kneaded to form a paste, which is impregnated in 0.2 to 1.0% glutaraldehyde solution in acetone to form a solid. Then the solidified material are separated from the acetonic solution by filtration without washing and finally dried to form immobilized glucose isomerase.

11 Claims, 1 Drawing Figure

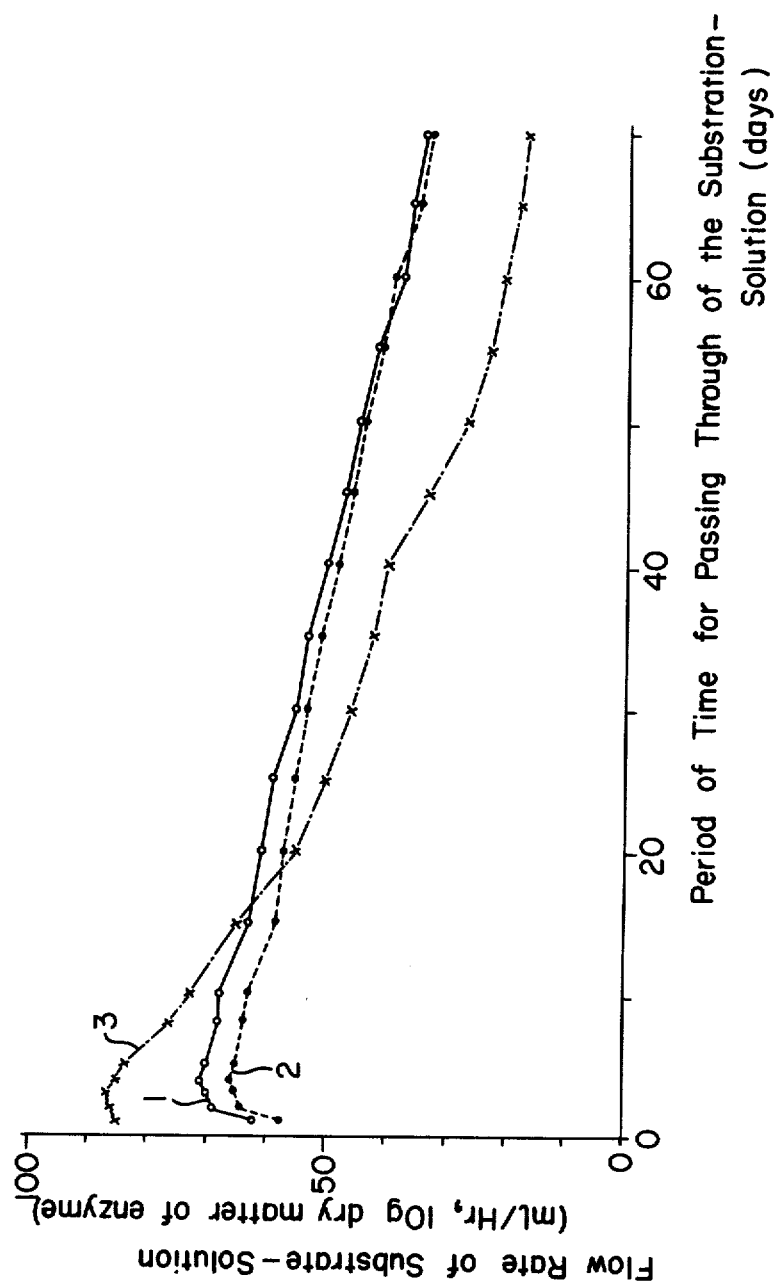

PROCESS FOR THE PRODUCTION OF IMMOBILIZED GLUCOSE ISOMERASE

BACKGROUND OF THE INVENTION

1. Field of the Invention

This invention relates to a process for the preparation of immobilized glucose isomerase by a method of immobilizing glucose isomerase in the state as contained in the microbial cell as it is.

2. Brief Description of the Prior Art

Hitherto, the industrial application of glucose isomerase was usually carried out by using the whole microbial cells containing glucose isomerase in themselves as enzyme preparation. In the state of native cells, however, the enzyme would dissolve out quite rapidly into the reaction solution, and so the upper limit of repetition times of usage was at most two or three considering from economic aspect.

Since it is required for saving the cost of enzyme to carry out the isomerisation with a smaller dosage of enzyme under a longer period of time, there are many disadvantages in such batch reaction, for examples, the requirement of a larger scale of reaction apparatus, the heavy coloration of isomerized syrup, and the expensive cost of purification of the colored syrup.

When the glucose isomerase is immobilized, glucose solution can be treated continuously by flowing through a layer of the immobilized enzyme in a reaction tower. In this case, the reaction time can be extremely shortened and accordingly the formation of coloring compounds and other impurities will be sharply reduced, and also the reaction apparatus and treating operation can be simplified. Thus a process using immobilized glucose isomerase is extremely advantageous for industrial isomerization of glucose.

Recently there have been examined various attempts for immobilizing glucose isomerase and conducting isomerization in a continuous process by the use of immobilized glucose isomerase, and proposed many methods thereof.

As for the immobilizing method of enzyme there can be cited a method wherein glucose isomerase is extracted from the microbial cells, then absorbed on a carrier such as ion-exchange resin (Japanese Open Laid Patent Specification No. Sho 50-53582) and activated alumina (Japanese Open Laid Patent Specification No. Sho 49-110887), a method wherein the extracted enzyme is entrapped in a synthetic fibre, a method wherein microbial cells containing glucose isomerase are treated with a cross-linking agent to solidify their cell walls, and also to combine with each other by the formation of cross-linkages among them (Japanese Open Laid Patent Specification No. Sho 49-92278), a method wherein microbial cells containing glucose isomerase are adsorbed on a special type of resin (Japanese Open Laid Patent Specification No. Sho 50-6774), or a method wherein microbial cells containing glucose isomerase are entrapped in a polymer, such as acrylamide gel, or collagen.

Among the above methods, those methods wherein glucose isomerase extracted from microbial cells is adsorbed on various carriers require a process for extracting enzyme from cells, because glucose isomerase is an intracellular enzyme, and usually also a process for purifying the extracted enzyme in order to prepare an immobilized enzyme of higher activity. Thus, a severe loss of enzyme is inevitable in these treatments.

Some methods for immobilizing microbial cells containing glucose isomerase have been known publicly in Japanese Open Laid Patent Specification No. Sho 49-92278, U.S. Pat. No. 3838007 and so on.

In Japanese Patent Publication No. Sho 50-37274, the disclosuure relates to a method for insolbilizing acid protease which is produced by a strain of Rhizopus and active in the acidic circumstance. However, when the pH value in the treatment is different from the adequate pH value in the enzymatic reaction, the activity of the enzyme is extremely reduced and the utilization of the preparation can not be made. Accordingly, it is impossible to apply the above method directly for immobilizing glucose isomerase which is produced by a strain of Actinomycetes and enzymatically active in the range of pH from neutral to alkaline, and even if the pH value in the treatment of immobilization is adjusted to a pH within a range where the activity of glucose isomerase is stable, immobilization of glucose isomerase cannot be attained effectively.

SUMMARY OF THE INVENTION

This invention was executed to provide a process for the preparation of a stable and solidified preparation of immobilized glucose isomerase which has a high enzymatic activity and a property of maintaining the activity for long period.

For immobilizing intercellular enzymes such as glucose isomerase, it is advantageous to apply the means for immobilizing the microbial whole cells containing the enzyme as it is without extracting the enzyme. When these methods are used, neither extraction nor purification of enzyme is required, and therefore it is possible to minimize the loss of the enzyme in the process of immobilization.

This invention relates to a process for immobilizing glucose isomerase in microbial cells by utilizing glutaraldehyde as cross-linking agent and gelatin and/or sodium caseinate as reinforcing agent. The invented process can be applied to those microorganisms belonging to genus Streptomyces as mentioned below, and to those belonging genus Actinomyces as well.

Examples of the glucose isomerase-producing microorganisms are as follows:

1. *Streptomyces phaeochromogenus* deposited with Bikoken Ferm-P 221
2. *Streptomyces fradiae* deposited with Bikoken Ferm-P 220
3. *Streptomyces albus*—ATCC 21132
4. *Streptomyces achromogenus*—ATCC 12767
5. *Streptomyces echinatus*—ATCC 21933
6. *Streptomyces wedmorensis*—ATCC 21230
7. *Streptomyces flovovirens*—ATCC 3320
8. *Streptomyces olivochromogenes*—ATCC 21114

All of them produce glucose isomerase in their cells.

The present invention will be particularly further explained.

In the first step of the invention, microbial cells of Actinomycetes having glucose isomerase activity is heated to a temperature of 70° to 80° C. in their culture medium adjusted to a pH of 6 to 9, then held for 1 to 20 minutes at the temperature, and after rapid cooling the microbial cells are collected by means of filtration or centrifugation. In the above treatment, proteases contained in the microbial cells are denaturated. Consequently, it is effective to prevent the autolysis of microbial cells and the hydrolysis of gelatin or sodium caseinate added latter as reinforcing agent.

The pH value of the culture medium should be adjusted in the range of 6 to 9 in order to keep the activity of glucose isomerase stable in the treatment after cultivation.

When the treatment of heating at 70° to 80° C. for 1 to 20 minutes is excluded, gelatin or sodium caseinate as reinforcing agent is undesirably degraded by protease contained in the microbial cells of Actinomycetes to result in a remarkable reduction of reinforcing effect. At a temperature above 80° C. glucose isomerase is also inactivated together with protease, and at a temperature below 70° C. protease is not thoroughly inactivated. In these cases, no desirable result can be obtained.

After the heating treatment, the culture medium containing microbial cells of Actinomycetes should be cooled rapidly in order to prevent the inactivation of glucose isomerase contained therein.

After the rapid cooling, microbial cells are harvested from the medium by filtration or centrifugation. By the above mentioned pretreatment before the freezing and thawing treatment, it is made possible to obtain an immobilized enzyme preparation having a hardness of high degree and a high activity of glucose isomerase by the use of the reinforcing agent in the dosage of only 2 to 10% of dry weight of the cells.

Then as secondary pretreatment, the cells are frozen and subsequently thawed. Since the cell walls are partially destroyed by this treatment, the cross-linking agent and the reinforcing agent can readily penetrate into the cells in the immobilization reaction.

In the next step, the addition of gelatin or sodium caseinate to the cells is made in the dosage of 2 to 10% of dry weight of the cells. Since gelatin or sodium caseinate acts as a reinforcing agent in the cross-linking reaction caused by glutaraldehyde, the stability of enzyme activity, the physical strength, and the bulk density of the immobilized preparation increase together. After the polymerization is carried out in an acetonic solution containing glutaraldehyde in a suitable concentration, the solidified particles of microbial cells are separated from the reaction solution without washing and dried under heating. During the period of drying, the further polymerization caused by the remaining glutaraldehyde proceeds. Thus, it is possible to minimize the loss of the enzymatic activity and simultaneously to maximize the effect of the immobilization reaction. An excellent preparation of immobilized glucose isomerase can be prepared by the use of the above mentioned series of process in combination.

In the process for thawing the frozen cells, it may be carried out either at normal temperature or, if required, under heating. In the process of making a paste, gelatin or sodium caseinate may be added to the thawed cells in a form of powder or solution. The amount of gelatin or sodium caseinate to be added is 2 to 10% of dry weight of cells.

If the amount of gelatin or sodium caseinate is lower than 2%, the hardness of the product will be undesirably low. If the said amount is more than 10%, the activity of the enzyme per unit weight of the product will be unfavourably low, even if the hardness thereof is almost the same with those of 2 to 10%.

For mixing gelatin with thawed cells, it is preferable to preheat the gelatin solution to a temperature of 60° to 70° C. The mixing is carried out at a normal temperature. If gelatin is used in powder form, it is preferable to add gelatin to the thawed cells which is previously heated to a temperature of 60° to 70° C. Sodium caseinate may be added in a form of aqueous solution dissolved in cold water or in a form of powder at a normal temperature without preheating the thawed cells.

The paste thus well kneaded may be extruded in an acetonic solution containing 0.2 to 1.0% of glutaraldehyde through a fine nozzle or thrown into the said acetonic solution in those shapes formed with the other means that are suitable enough for the permeation of glutaraldehyde and the cross-linking reaction to be accomplished satisfactorily. The paste changes into s solid form in 5 minutes on standing. Then the reaction solution is gently stirred for 5 to 10 minutes to proceed the reaction sufficiently. In this process, it is preferable to circulate only the solution alone with a pump in order to prevent the destruction of the solid as best one may.

After completion of the reaction, the solidified microbial cells are recovered from the reaction solution by filtration or centrifugation. The solidified microbial cells are dried at a temperature of 45° to 50° C. under heating to form the product, whereby by the action of remaining glutaraldehyde after polymerization is further proceeded to give an immobilized enzyme preparation which has a high physical strength, a high bulk density and also a stabilized activity. The dried solid, if required, regulated by crushing and/or filtering off micro powder in order to prepare the final product.

However, if the paste composed of microbial cells and gelatin or sodium caseinate is supplied into acetonic solution containing glutaraldehyde in a form of particles of suitable size, the crushing treatment as said above is not necessary. It is essential to adjust the concentration of glutaraldehyde used as cross-linking agent within a range of 0.2 to 1.0%. If the concentration is lower than 0.2%, the immobilization will not sufficiently be attained, and the resulting product will be inferior in the stability of the activity and in the physical strength. If it is higher than 1.0%, the strength of particles will be increased, but the activity of the product will be reduced and the deterioration of the activity during the storage will be exceeded. When the solidification is carried out in the range of the concentration according to the present invention, it is not required to remove glutaraldehyde from the solid by washing with water. Furthermore the remaining glutaraldehyde will react in the after polymerization reaction proceeding in the drying process with heating to result in the increase of the stability of the activity, bulk density and physical strength of the product without lowering the activity.

According to the process of the invention the enzymes are firmly confined in the microbial cells and simultaneously microbial cells are strongly combined with each other and accordingly particles having stable activity and sufficient physical strength can easily be obtained.

According to the invention by using the immobilization-conditions by suitably combining the pretreatments of the glucose isomerase-containing microbial cells with the process wherein gelatin or sodium caseinate is used as reinforcing agent, a stabilized, immobilized enzyme which has a high activity and sufficient physical strength and property of maintaining the activity for long period can be obtained.

When the immobilized glucose-isomerase in particle form produced by the process according to the invention is used in a column by filling therein in a layer and the substrate solution is passed continuously through in the said column, the reaction can be effected in a rapid flow rate of the substrate solution and the time for contacting the enzyme with said substrate will be shortened because the activity of the layer per unit volume is higher. According to the process of the invention, therefore, the formation of colored products and other degradation products is minimized as compared with the known art and accordingly the cost for refining is largely saved. Since the enzyme preparation is excellent in its properties of the stability of the enzymatic activity and the hardness of the particles, the usable period of the preparation is quite advantageously long in the industrial use. These advantages as stated above have not at any rate been attained according to the prior art unless by the use of the present invention.

An immobilized glucose isomerase preparation prepared by the process of the present invention is excellent as stated above. The fact is further illustrated by the annexed FIGURE. In the FIGURE the isomerization capacity of each enzyme preparation is shown, thus (1) in the FIGURE represents the capacity of the enzyme preparation according to Example 1. (2) represents that of the enzyme preparation according to Example 2. (3) represents that of the comparative enzyme preparation prepared without addition of the reinforcing agent.

The isomerization capacity of the immobilized enzyme preparation is represented by the flow rate of the 40 w/w % glucose solution containing 0.4 m mol. $MgSO_4$ and 4 m mol $Na_2SO_3$ per liter; adjusted at pH 8.2 with $Na_2CO_3$) so as to obtain the isomerization ratio of 45% when said glucose solution is passed through the column at 65° C., which being filled with 10 g, as dry matter, of the immobilized enzyme preparation. A larger figure of the flow rate represents a higher activity of the enzyme.

As shown in the results of the test stated above, the preparation prepared according to Example 1, wherein the addition of gelatin is made and the one prepared according to Example 2, wherein the addition of sodium caseinate is made, had quite larger stabilities when compared with the preparation of the Comparative Example wherein no addition of gelatin or sodium caseinate is made. The enzymatic activity of the preparation prepared according to the invention did not undergo a change during the first ten days and after then the said activity was reduced by half in the period of 60 days. The amount of glucose isomerized in a ratio of 45% during these total 70 days was 42 kg per 10 g, as dry matter, of the enzyme preparation in the case comprising the addition of gelatin, and 40 kg in the case comprising the addition of sodium caseinate. These values correspond to one and half times of 27 kg, in the case of the enzyme preparation, comprising no addition, wherein the amount of glucose was treated durin 40 days, in which half the enzimatic activity of this preparation reduced by half.

In the comparative example, the immobilized enzyme preparation was prepared in the same manner as described in Example 1, except that gelatin is not added.

Immobilized enzyme preparations were prepared by using egg-alubumin and glutenin instead of gelatin and sodium caseinate in the same manner as described in Example 1.

These were, however, considerably inferior to those prepared accordng to the present invention in the hardness of the particles, especially in moistened state, as shown in Table 1. The bulk density of the immobilized preparation containing gelatin or sodium caseinate prepared according to the invention was larger than that of the preparation containing egg-albumin or glutenin. The importance of selecting the protein used in the present methods may be obviously convinced by reviewing these results stated as above, and this is the reason that the novelty of the present invention is obvious.

Increase of the bulk density of the immobilized preparation makes the property of sedimentation favorable in the procedure of charging the preparation into the reaction column and also results more essentially in an elevation of the activity per unit volume. Accordingly the period for contacting the substrate with the enzyme may as much as be shortened, in other words, it is possible to pass through the solution in a more rapid rate and also to reduce the size of the reaction column. These are quite advantageous for industrial use.

The relations between the amount of the addition of gelatin or sodium caseinate and the hardness and bulk density of enzyme particles are shown in Table 2. The amount of addition is suitably in a range of 2–10%, preferably 5–10%, based on the weight of the dry matter.

Among the immobilized enzyme preparations disclosed in Table 2, the preparation containing gelatin is prepared in the same manner as described in Example 1 and the others are also prepared by the same manner as described in Example 1, except the prescribed amount of gelatin was used in each case.

TABLE 1

| Protein Added To the Paste | Dry Matter (%) | Bulk Density *1 (gd.m./ml) | Hardness of Particles | |
|---|---|---|---|---|
| | | | in Dry State (kg) | in Wet State (kg) |
| Gelatin | 87.5 | 0.257 | 3.5 | 1.1 |
| Sodium Caseinate | 87.7 | 0.244 | 4.0 | 0.9 |
| Egg-Albumin | 87.5 | 0.256 | 3.0 | 0.4 |
| Glutenin | 87.2 | 0.169 | 2.8 | 0.3 |
| None | 87.3 | 0.80 | 0.1 | 0.1 |

*1 Measured in the state where the substrate solution is passing through in the column.
*2 Hardness of the particle is obtained by measuring the load (kg) required for crushing a particle of 20–40 mesh particles by means of Texturometer GTX Type 2 (Zenken KK).
Measuring conditions are shown as follows:
Plunger: Aluminium alloy, dia. 13 m/m
Platform: Flat plate
Clearance: 0.35 m/m
Voltage: for dry samples 1.5 V, for Wet samples 3.0 V
Strain-gauge-arm: Hard-arm Samples in wet state in prepared by impregnating the dry samples in 40 w/w % glucose solution containing (0.4 m mol $MgSO_4$ and 4 m mol $NO_2SO_3$ per liter, adjusted at pH 8.2 with $Na_2CO_3$) at 65° C. during a whole day.

TABLE 2

| Amount Of Gelatin Added To The Paste On Dry Base (%) | Dry Matter (%) | Bulk Density *1 (gd.m/ml) | Initial Flow *3 Rate Of The Substrate Solution (ml/10gdm. Hr) | Hardness Of Particles *2 | |
|---|---|---|---|---|---|
| | | | | In Dry State (kg) | In Wet State (kg) |
| 0 | 87.3 | 0.180 | 86.9 | 2.6 | 0.1 |
| 2.2 | 87.5 | 0.241 | 73.0 | 3.3 | 0.7 |
| 4.3 | 87.5 | 0.249 | 69.1 | 3.4 | 1.1 |
| 8.5 | 87.5 | 0.257 | 70.0 | 3.5 | 1.1 |

*1 Same as Table 1
*2 Same as Table 1
*3 The initial flow rate of the substrate solution is represented by the flow rate by which the isomerization ratio of 45% can be obtained when 40 w/w % glucose solution (containing 0.4 m mol $MgSO_4$ and 4 m mol $Na_2SO_4$ per liter; adjusted at pH 8.2 with $Na_2CO_3$) is passed through a column comprising 10 g in dry base of freshly prepared immobilized enzyme preparation at 65° C.

A process for immobilizing of enzyme comprising the use of protein and the formation of cross-linkage with glutaraldehyde is described in U.S. Pat. No. 3,838,007 (Sept. 24, 1974). However, the said process is quite different from the present invention in the technical contents of the invention. Thus, according to the said U.S. Pat. No. 3,838,007 the protein is utilized as gelling agent to make the enzyme in particle form. In the procedures disclosed by the Patent, the mixture of enzyme and, so to say, gelling protein is suspended in an organic liquid poorly miscible or immiscible in water and then treating the resulting suspension by cooling or heating to effect gelatin thereof in a particle form and then treated with a cross-linking reagent to produce a water insoluble enzyme preparation.

On the contrary, protein, i.e. gelatin or sodium caseinate used according to the present invention, does not play as gelling agent, whereas this is used in the claimed amount for the purpose of obtaining excellent hardness and stability of enzymatic activity of the immobilized enzyme particles to be produced. Therefore, the amount of protein to be added based on the amount of enzyme in the present invention is much far smaller than that in the U.S. Patent said above. Contrary to the process according to said U.S. Patent, according to the present invention two treatments are carried out simultaneously in acetonic solution containing glutaraldehyde. One of them is the treatment for the formation coagulated particles from a paste by partial dehydration with acetone which is an organic solvent and freely miscible with water, and the other is the treatment for the cross-linking reaction performed by glutaraldehyde included in the acetonic solution. In this step there are important parts in the process of the present invention. Difference of the present invention from the invention of said U.S. Pat. No. 3,838,007 is clear and admits no further discussion from the facts as stated above in the difference of the purpose of the use of protein and the difference in the use of a poorly water miscible or water immiscible organic solvent in the said U.S. Patent contrary to the use of a freely water-immiscible, organic solvent such as aceton in the process of the present invention.

BRIEF EXPLANATION OF THE FIGURE

The attached FIGURE is a chart in which the lives of the enzyme preparations according to Examples 1 and 2 and a comparative preparation are compared, and in which the flow rates of substrate solution (glucose 40%, by weight by weight, 0.4 m mol $MgSO_4/l$, 4 m mol $Na_2SO_3/l$; pH 8.2) for obtaining 45% isomerization were platted as a function of time.

In the FIGURE, (1) represents a curve which shows the life of the enzyme preparation according to Example 1, wherein gelatin was added as reinforcing agent. (2) represents a curve which shows the life of the enzyme preparation according to Example 2, wherein sodium caseinate was added as reinforcing agent. (3) represents a curve which shows the life of the enzyme preparation according to comparative process, wherein no reinforcing agent was added.

EXAMPLE 1

Then liters of the cultured medium which was obtained by culturing Streptomyces phaeochromogenus (deposited with Bikoken) (Ferm-P 221) in the liquid medium containing D-xylose under aerobic conditions is adjusted at the pH value of 7.5, then heated to the temperature of 75° C. and maintained at the same temperature for 5 minutes and then cooled rapidly to 20° C., which is treated by centrifuge to collect microbial cells. The obtained cells were transported on a Buchner funnel precoated with diatomaceous earth and washed with deionized water under reduced pressure. After draining off the water completely, microbial cells were then stripped off from diatomaceous earth and frozen by standing over night in a polyethylene bag in a freezer at −20° C. The weight of obtained frozen cells was 135 g, its dry matter was 28%, and its glucose isomerase activity was 820 unit/g. With respect to the activity of glucose isomerase, 1 unit of activity corresponds to the enzyme activity which is able to form 1 mg of fructose during 1 hour in the reaction mixture containing 0.1 mol dextrose, 0.005 mol $MgSO_4$ and 0.5 mol phosphate buffer, pH 7.0, at 70° C.

The frozen mass of cells is treated by thawing in a 300 ml of beaker at room temperature, then 3.2 g of gelatin dissolved in 30 ml of warm water is added and kneaded well with spoon to result in a homogeneous paste and an injector having a nozzle of 0.8 mm in dia is charged with the obtained paste.

Four hundred milliliters of acetone (99%) and 8 ml of 25% aqueous glutaraldehyde solution is mixed under stirring in a 1 l of beaker, then by the addition of a trace of 1 N NaOH the pH value thereof is adjusted to 7.5. Into this solution the whole amount of the cellular paste obtained as above is extruded within about 5 minutes from the nozzle of injector, after standing for 5 minutes the extruded paste is changed into a solid form in form of a cord and then the solution is stirred with a glass rod for further 10 minutes and the mixture is filtered under reduced pressure on a filter paper using Buchner's funnel. After squeeze out of aceton from the filtered residue on the filter by slightly pressing, the obtained cord is spreaded on a dish for 1 hour to let acetone evaporate and then dried in a thermostatic oven at 47° C. for 3 hours.

The dried substance is crushed with an empty bottle to form pellets in a short rod-form and the obtained pellets are treated with 40 mesh sieve to remove any micro powder and thus 40 g of immobilized glucose isomerase preparation is obtained. The product contains 12.5% of moisture.

As a substrate solution for isomerization-reaction a solution containing 40% by weight by weight glucose, 0.4 m mole MgSO$_4$/l, 4 m mole Na$_2$SO$_3$/l and adjusted at pH 8.2 with Na$_2$CO$_3$ is prepared.

11.42 g (corresponds to 10.0 g of dry matter) of solidified enzyme preparation which had been previously impregnated in the said substrate solution during 1 hour were transferred into a double walled tube having 20 mm of inner diameter, then the substrate solution was passed through therein at a starting flow rate of 62 ml/Hr under recycling of warm water of 65° C. in the jacket. With respect to the isomerized solution glucose was assayed by the glucose-oxidase method and also fructose was assayed by the cystein-carbazole method and from these results the isomerisation ratio was obtained. By controlling the flow rate so as to obtain about 45% of isomerization ratio the reaction test was carried out during 70 days and the results obtained are shown below:

| days | flow rate (ml/Hr) |
|---|---|
| 1 | 62 |
| 5 | 70 |
| 10 | 68 |
| 15 | 63 |
| 20 | 61 |
| 25 | 59 |
| 30 | 55 |
| 35 | 53 |
| 40 | 50 |
| 45 | 47 |
| 50 | 45 |
| 55 | 42 |
| 60 | 38 |
| 65 | 36 |
| 70 | 34 |

As shown in the data the activity of the enzyme did not change during initial ten days from the start, then after 60 days the activity of the enzyme was reduced by half and the amount of glucose having been treated by 45% of isomerisation ratio during total 70 days was 42 kg. Initial volume of the enzyme bed in the column was 40 ml and after 70 days it was 44 ml and accordingly after 70 days the contacting time of the substrate solution was less than two hours. The used enzyme preparation taken out from said column was tested with respect to its hardness, and was found to be sufficiently hard and might be further used for a long period of time.

EXAMPLE 2

In this example enzyme preparation was prepared as same manner as described in Example 1, except that 3.2 g of sodium caseinate was used instead of gelatin. 40 g of the enzyme preparation was obtained and it contained 12.3% of moisture.

The isomerization reaction with respect to the said preparation was carried out as same manner as described in Example 1 and the results were shown below:

| days | flow rate (ml/Hr) |
|---|---|
| 1 | 57 |
| 5 | 65 |
| 10 | 63 |
| 15 | 58 |
| 20 | 57 |
| 25 | 55 |
| 30 | 53 |
| 35 | 51 |
| 40 | 48 |
| 45 | 46 |
| 50 | 44 |
| 55 | 41 |
| 60 | 38 |
| 65 | 35 |
| 70 | 33 |

As shown in the data the activity of the enzyme did not change during initial ten days from the start, then after 60 days it was reduced by half and the amount of glucose having been treated by 45% of isomerization ratio during total 70 days was 40 kg. Initial volume of the enzyme bed in the column was 42 ml and after 70 days it was 46 ml and accordingly after 70 days the contacting time of the substrate solution was less than two hours. The used enzyme preparation taken out from said column was treated with respect to its hardness and was found to be sufficiently hard and might be further used for a long period of time.

What is claimed is:

1. A process for the preparation of immobilized glucose isomerase, which comprises heating microbial cells of Actinomycetes which have glucose isomerase activity, at a temperature of 70°–80° C. for 1–20 minutes in a culture medium adjusted to a pH value of 6–9, rapidly cooling the heated medium, collecting the microbial cells by filtration or centrifugation, treating the collected cells with freeze and thawing method, adding gelatin or sodium caseinate in an amount of 2–10% based on the weight of the cells in dry base, forming a paste by kneading the obtained mixture, impregnating the formed paste in acetone which contains 0.2–1.0% of glutaraldehyde to result in solidification, removing the solvent from the solidified microbial cells by filtration without washing and drying the filtered cells to produce immobilized glucose isomerase preparation.

2. A process according to claim 1, wherein a microbe of Actinomycetes having isomerase activity is selected from the strains of genus Streptomyces.

3. A process according to claim 2, wherein a microbe is selected from the group consisting of *Streptomyces phaeochromogenus* (deposited with Bikoken Ferm-P 221) *Streptomyces fradiae* (deposited with Bikoken Ferm-P 220), *Streptomyces albus* (ATCC 21132), *Streptomyces achromogenus* (ATCC 12767), *Streptomyces echinatus* (ATCC 21933), *Streptomyces wedmorensis* (ATCC 21230), *Streptomyces flovovirens* (ATCC 3320) and *Streptomyces olivochromogenes* (ATCC 21114).

4. A process according to claim 1, wherein gelatin is added as solution at a temperature of 60°–70° C.

5. A process according to claim 1, wherein gelatin is added in a powder form to a mass of microbial cells which was previously warmed to 60°–70° C.

6. A process according to claim 1, wherein sodium caseinate is added as aqueous solution.

7. A process according to claim 6, wherein sodium caseinate powder is added at a normal temperature.

8. A process according to claim 1, wherein said paste is extruded in acetone solution containing 0.2–1.0% of glutaraldehyde.

9. A process according to claim 1, wherein said paste is added to acetone containing 0.2–1.0% of glutaraldehyde by shaping said paste in a form of such a size that is suitable for the permeation of glutaraldehyde into the said paste to be made readily.

10. A process according to claim 1, wherein obtained immobilized glucose isomerase product is dried at a temperature of 45°–50° C.

11. Immobilized glucose isomerase preparation prepared by the process as claimed in claim 1.

* * * * *